United States Patent [19]

Watkin et al.

[11] Patent Number: 5,485,841
[45] Date of Patent: Jan. 23, 1996

[54] ULTRASONIC LUNG TISSUE ASSESSMENT

[76] Inventors: Kenneth L. Watkin, 258 Hollis Road, Beaconsfield, Quebec, Canada, H9W 2M7; Peter T. Macklem, 3470 Redpath, #207, Montreal, Quebec, Canada, H3G 2G3

[21] Appl. No.: 388,302

[22] Filed: Feb. 14, 1995

[51] Int. Cl.⁶ ........................................................ A61B 8/00
[52] U.S. Cl. ........................................................ 128/660.01
[58] Field of Search ........................ 128/660.01, 660.06, 128/660.87, 661.01

[56] References Cited

U.S. PATENT DOCUMENTS

| | | | |
|---|---|---|---|
| 4,431,007 | 2/1984 | Amazeen et al. | 128/661.01 X |
| 5,178,147 | 1/1993 | Ophir et al. | 128/661.03 X |
| 5,331,947 | 7/1994 | Shturman | 128/662.06 X |

FOREIGN PATENT DOCUMENTS

| | | |
|---|---|---|
| 794486 | 1/1981 | U.S.S.R. . |
| 1718821 | 3/1992 | U.S.S.R. . |

OTHER PUBLICATIONS

Wells, P. N. T., "Biomedical Ultrasonics", Academic Press N.Y. ©1977, pp. 304–305.

*Primary Examiner*—Francis Jaworski
*Attorney, Agent, or Firm*—Swabey Ogilvy Renault

[57] ABSTRACT

A diagnostic method and apparatus for assessing lung tissue during breathing, transmits ultrasonic radiation into the lung tissue; reflected or echo radiation, is reflected dynamically by air spaces in the tissue; a signal is developed from the reflected or echo radiation as a dynamic real-time measure of parameters of the air spaces, particularly size and density or number, indicative of the state of the lung tissue.

10 Claims, 3 Drawing Sheets

ULTRASONIC LUNG TISSUE ASSESSMENT

BACKGROUND OF THE INVENTION i) Field of the Invention

This invention relates to a diagnostic method and apparatus for assessing lung tissue of a living subject; more especially the invention is concerned with such a method and apparatus employing ultrasonic radiation.

ii) Description of Prior Art

Ultrasound has been used in medical, industrial and other environments, and various systems and methods have been employed.

Single element ultrasound systems have been used to pass ultrasonic waves into the human body, for example, as part of an evaluation of the state of health of body organs.

These systems provide real-time, time of flight, reflectance images of the body organs.

Ultrasound systems have also been employed in therapy.

Various proposals have been made for use of reflectance ultrasonic assessing of the lung, but none of these proposals permit real-time assessing, so as to be effective with continuous breathing.

There is a particular need for diagnosis aids which will provide medical diagnostic information relating to diseases and disorders of the lung, for example, emphysema, asthma and disorders resulting from use of tobacco products.

At present diagnosis of the number and size of airspaces in the human lung requires the use of costly medical imaging equipment such as CT or MRI. With such equipment it is not possible to assess the lungs dynamically, in other words it is not possible to assess the changes in the airspaces during breathing.

SUMMARY OF THE INVENTION

It is an object of this invention to provide a diagnostic method and apparatus for assessing parameters of the air spaces in the lung tissue during breathing, particularly the size and the number or density of such airspaces.

In accordance with one aspect of the invention there is provided a diagnostic method for assessing lung tissue of a living subject comprising: transmitting ultrasonic radiation from an ultrasonic source into the lung tissue, during breathing by the subject, receiving reflected ultrasonic radiation, reflected dynamically by air spaces in the tissue, and developing a signal from the reflected ultrasonic radiation as a dynamic real-time measure of parameters of the airspaces indicative of the state of the lung tissue.

In accordance with another aspect of the invention there is provided a diagnostic apparatus for assessing lung tissue of a living subject comprising: a source of ultrasonic radiation adapted to transmit ultrasonic radiation into the lung tissue, receiving means for reflected ultrasonic radiation, dynamically reflected by air spaces in the lung tissue, and signal developing means for developing a signal from the reflected ultrasonic radiation as a dynamic real-time measure of parameters of the airspaces indicative of the state of the lung tissue.

DETAILED DISCLOSURE OF THE INVENTION

In the diagnostic method of the invention the ultrasonic radiation is transmitted continuously or continually as a pulsed beam, into the lung tissue; the ultrasonic radiation passes through the tissue but acoustic discontinuities in the tissue, including the airspaces, reflect the ultrasonic radiation as an ultrasonic echo.

A signal is developed from the echo, in real-time and as a measure of the size and number or density of the airspaces from which the state of the lung tissue can be determined.

In particular the echo may be converted to a power spectral analysis, in which the different frequencies indicate different sizes and shapes of airspaces, while the amplitude indicates the strength and density of the airspaces.

The pulsed beam is produced by a voltage output to generate the pulses of ultrasonic radiation.

The invention may, in particular, take the form of a non-invasive echo-ultrasonic method for determining in vivo the size and density of the airspaces in the lung tissue, from the external chest wall of the chest cavity housing the lungs during breathing.

The apparatus of the invention may be portable in nature and in a particular embodiment has an ultrasound transducer for lung tissue imaging between adjacent ribs, which transducer develops the pulsed beam; a digital signal processing based pulse/echo circuitry, a graphic display panel and a printer.

In operation the transducer is placed between adjacent ribs on the external wall of the chest cavity, a pulsed beam of ultrasonic radiation is transmitted between the ribs into the lung tissue; the circuits rapidly average the reflected or echo beam. The digital signal processing circuitry applies spectra analysis techniques to determine the number and size of the air spaces as a function of time. The real-time graphic display provides a continuously or continually up-dated curve which may be printed.

DESCRIPTION OF PREFERRED EMBODIMENTS WITH REFERENCE TO DRAWINGS

Figure 1:
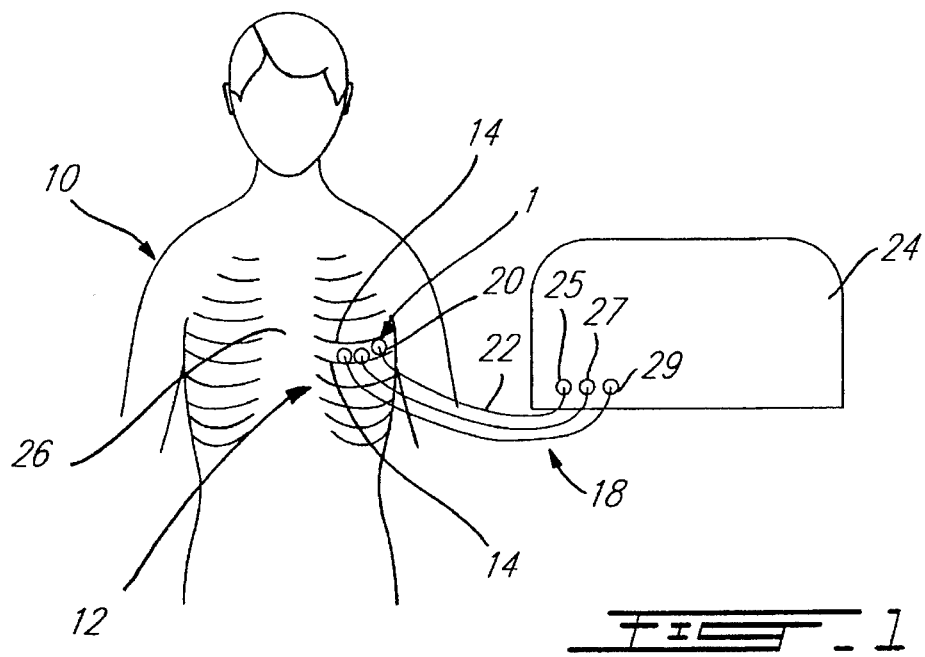
FIG. 1 illustrates schematically the use of the diagnostic apparatus of the invention.

With further reference to FIG. 1 a patient 10 being diagnosed has a chest wall 12 and ribs 14 of a thoracic chest cavity 26.

Ultrasonic assessing apparatus 18 includes source/receiver 20 for transmitting pulsed ultrasonic radiation and receiving the echo radiation, connected by an electrical connection 22 to associated components shown generally at 24, at an electrical input 25

The components shown generally at 24 also have electrical inputs 27 and 29 for electrical connection of second and third source/receivers 20. In FIG. 1 three source/receivers 20 are illustrated, but it will be understood that a single such source/receiver 20, or some other plurality, may be employed in the evaluation of the state of the lung of a subject, each source/receiver 20 of the plurality being placed between a pair of adjacent ribs 14 on the chest wall 12.

Figure 2:
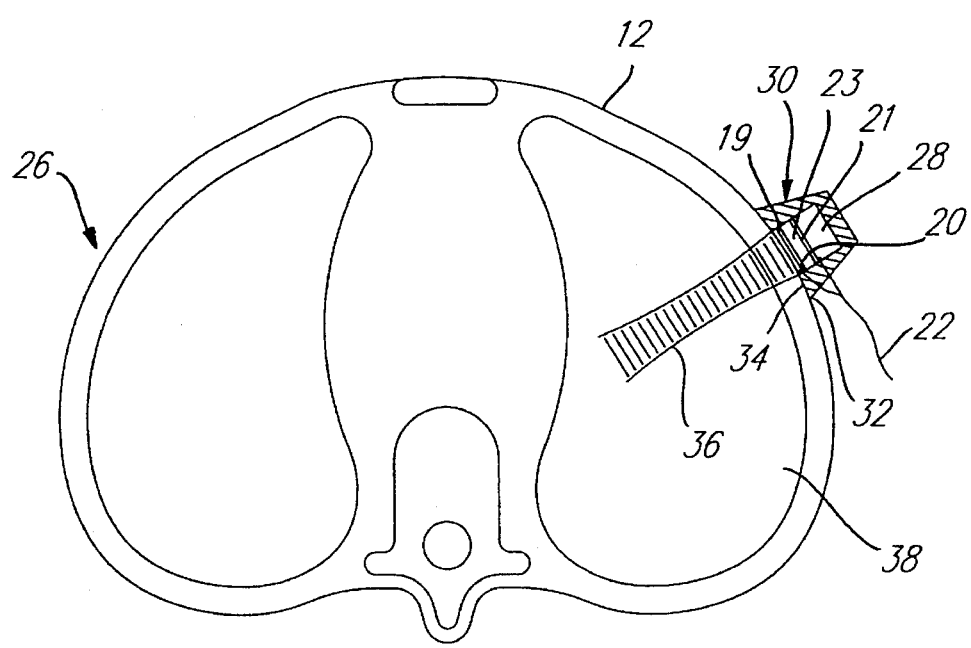
FIG. 2 illustrates schematically transmission of ultrasonic radiation into the lung tissue.

With further reference to FIG. 2, there is shown a schematic of the transverse section of the thoracic cavity 26. The source/receiver 20 has electrodes 19 and 21 separated by a piezoelectric crystal 23, and an airbacked region 28 and is contained in a housing 30. Electrical connection 22 is electrically connected to the electrodes 19 and 21.

Housing 30 is disposed or attached to the surface of the chest wall 12 between a pair of ribs 14, as shown in FIG. 1, with a sonically conducting medium, for example, gel 32 between the source/receiver 20 and the skin 34 of chest wall 12.

A pulsed ultrasonic beam 36 travels through the gel 32 and the skin 34. Beam 36 passes through the muscles (not shown) between adjacent ribs 14 and into the lung tissue 38.

Reflections from the muscles and lungs are received by the source/receiver 20.

The airbacked region 28 dampens the ultrasonic pulses developed in a direction away from the chest wall 12.

Figure 3:
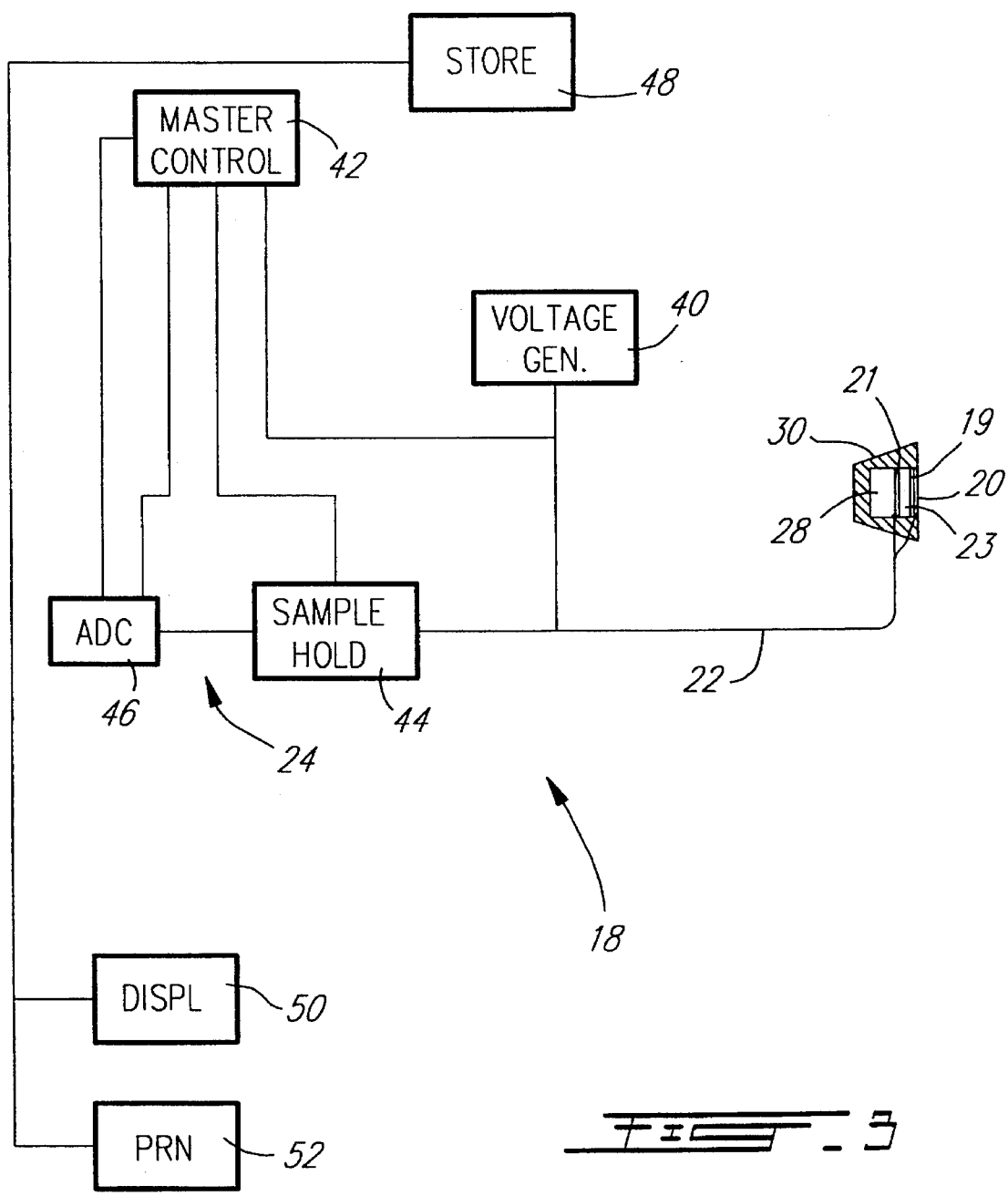
FIG. 3 is a block diagram of the apparatus of the invention.

With further reference to FIG. 3, apparatus 18 includes source/receiver 20, electrical connection 22 and components 24. Components 24 include a voltage generator 40, a master digital signal processing control system 42 and a sample and hold system 44 which controls sends and receives the pulsed/echo ultrasonic radiation.

An analog-digital conversion circuit 46 and digital storage component 48 are also controlled by master control system 42.

The apparatus 18 further includes a display component 50 and a printer 52.

In operation, while the subject or patient is breathing, pulse-echo signals are created using the master control system 42 to control the output of voltage generator 40. Voltage generator 40 sends a pulse to the source/receiver 20 creating an ultrasonic acoustic wave propagating into the chest.

The acoustic wave is reflected by the discontinuities in the lung tissue. The reflected ultrasonic radiation or echo is detected by the source receiver 20 and a signal responsive thereto is routed to the sample and hold system 44. This signal is digitized for further signal processing and storage.

The master control system 42 performs spectral analysis on the received signal and stores the processed signal in the digital storage components 48. The master control system 42 updates the display component 50 in real-time. The master control system permits printing by printer 52 of the display on display component 50.

Figure 4:
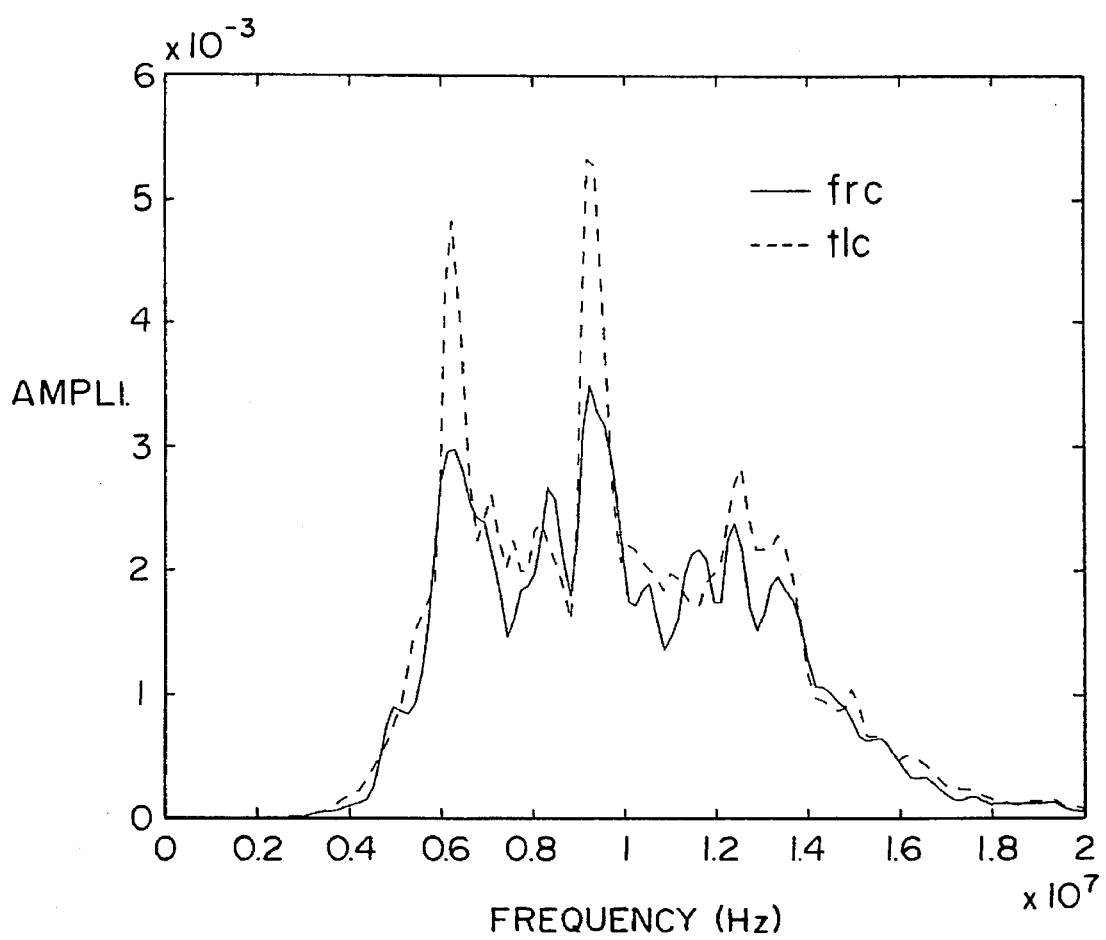
FIG. 4 is a power spectral density plot generated by the method of the invention for a healthy adult male.

FIG. 4 demonstrates the results of power spectral analysis applied to a healthy adult male. The source/receiver 20 was directed between the ribs into the lung tissue as illustrated in FIG. 2. The signal reflected from approximately 3.5–4.5 cm from the chest wall surface was analyzed subsequently. Presented in FIG. 4 are the power spectral density plots from the sampled region at different lung volumes (Functional Residual Capacity and Total Lung Capacity. Different frequencies reflect different sizes and shapes of airspaces while the amplitude reflects the strength and density of the airspaces. Further spectral analysis will yield the density of the airspaces. As can be seen in this figure at different lung volumes there are differences in both the size/shape and density of the airspace. In the embodied apparatus, the digital signal processing component will convert the spectral data into size/density values which are updated rapidly enough to display the time varying change in density and size during breathing.

The ultrasonic radiation in the invention typically has a frequency of at least 1 mega Hertz. In the pulse/echo operation, the duration of the successive pulses is very short, however, the system is controlled so that the echo or reflected radiation pulse is received at the receiver between sequential transmitted pulses.

The echo radiation comprises acoustic impedance mismatch from which reflection by muscle and lung tissue are subtracted to derive a signal indicative of the reflectance from the discontinuities including the airspaces of the lung tissue.

The apparatus and method of the invention have particular application as part of a relatively inexpensive screening of subjects to isolate those subjects requiring the high cost imaging studies.

While the source/receiver 20 is shown as a single unit the source and receiver could be separate elements placed at different locations, the receiver thus receiving radial scatter of the reflected radiation.

We claim:

1. A non-invasive diagnostic method for determining the state of lung tissue housed in a chest cavity of a living subject comprising:

transmitting ultrasonic radiation from an ultrasonic source disposed externally of an external chest wall of the chest cavity, through the chest wall and into the lung tissue, during breathing by the subject, receiving reflected ultrasonic radiation, reflected dynamically by airspaces in the tissue, and developing a signal from the reflected ultrasonic radiation as a dynamic real-time measure of parameters of the airspaces indicative of the state of the lung tissue.

2. A method according to claim 1, wherein said parameters comprise size dimensions and densities of airspaces reflecting the reflected radiation.

3. A method according to claim 2, in which said ultrasonic radiation is transmitted continuously into the lung tissue, reflected radiation is received continuously and the signal is developed continuously.

4. A method according to claim 2 in which said ultrasonic radiation is transmitted continually into the lung tissue, the reflected radiation is received continually and the signal is developed continually.

5. A method according to claim 3, wherein said ultrasonic source is disposed on said external chest wall of the subject to transmit said radiation into the chest cavity housing the tissue.

6. A method according to claim 1, wherein the transmitted ultrasonic radiation is a pulsed ultrasonic radiation beam.

7. A diagnostic apparatus for non-invasive determination of the state of lung tissue housed in a chest cavity of a living subject comprising:

a source of ultrasonic radiation adapted to be disposed externally of an external chest wall of the chest cavity to transmit ultrasonic radiation through the chest wall and into the lung tissue, receiving means for reflected ultrasonic radiation adapted to receive reflected ultrasonic radiation dynamically reflected by airspaces in the lung tissue, and signal developing means for developing a signal from the reflected ultrasonic radiation as a dynamic real-time measure of parameters of the airspaces indicative of the state of the lung tissue.

8. An apparatus according to claim 7, wherein said source and said receiving means are in a common housing.

9. An apparatus according to claim 8, further comprising a voltage generator operably connected to said source and receiving means, and control means for controlling output of the voltage generator to create a pulsed ultrasonic radiation beam.

10. An apparatus according to claim 7, wherein said parameters comprise size dimensions and densities of airspaces reflecting the reflected radiation.

* * * * *

UNITED STATES PATENT AND TRADEMARK OFFICE
CERTIFICATE OF CORRECTION

PATENT NO. : 5,485,841
DATED : January 23, 1996
INVENTOR(S) : Kenneth L. Watkin and Peter T. Macklem It is certified that error appears in the above-identified patent and that said Letters Patent is hereby corrected as shown below:

At column 3, line 55, after "Total Lung Capacity" insert

--- ) ---.

Signed and Sealed this

Ninth Day of July, 1996

Attest:

BRUCE LEHMAN

Attesting Officer       Commissioner of Patents and Trademarks

UNITED STATES PATENT AND TRADEMARK OFFICE
CERTIFICATE OF CORRECTION

PATENT NO. : 5,485,841

DATED : January 23, 1996

INVENTOR(S) : Kenneth L. Watkin and Peter T. Macklem

It is certified that error appears in the above-indentified patent and that said Letters Patent is hereby corrected as shown below:

On the title page, insert the following:
   [73] McGill University, Montreal, Quebec, Canada.

Signed and Sealed this

Third Day of September, 1996

Attest:

BRUCE LEHMAN

Attesting Officer     Commissioner of Patents and Trademarks